United States Patent
Nelson et al.

(10) Patent No.: US 12,331,010 B2
(45) Date of Patent: Jun. 17, 2025

(54) METHOD AND SYSTEM FOR OXIDIZING CUMENE AND HYDROCARBONS

(71) Applicant: SABIC GLOBAL TECHNOLOGIES B.V., Bergen op Zoom (NL)

(72) Inventors: Mark Erik Nelson, Mt. Vernon, IN (US); Arkady Samuilovich Dykman, St. Petersburg (RU); Andrey Vladimirovich Zinenkov, St. Petersburg (RU)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 409 days.

(21) Appl. No.: 17/795,723

(22) PCT Filed: Mar. 2, 2021

(86) PCT No.: PCT/US2021/020445
§ 371 (c)(1),
(2) Date: Jul. 27, 2022

(87) PCT Pub. No.: WO2021/178393
PCT Pub. Date: Sep. 10, 2021

(65) Prior Publication Data
US 2023/0072344 A1    Mar. 9, 2023

(30) Foreign Application Priority Data
Mar. 3, 2020 (RU) ............................... 2020109437

(51) Int. Cl.
C07C 407/00    (2006.01)
(52) U.S. Cl.
CPC ................ *C07C 407/003* (2013.01)
(58) Field of Classification Search
CPC ........................... C07C 407/00; C07C 407/03
See application file for complete search history.

(56) References Cited

U.S. PATENT DOCUMENTS

| | | | |
|---|---|---|---|
| 7,393,984 B1 | 7/2008 | Zakoshansky et al. | |
| 8,461,397 B2* | 6/2013 | Lattner | C07C 409/08 |
| | | | 568/338 |
| 8,729,315 B2* | 5/2014 | Burattini | C07C 407/00 |
| | | | 568/802 |
| 8,952,202 B2 | 2/2015 | Purola | |
| 8,975,444 B2* | 3/2015 | Purola | C07C 407/00 |
| | | | 568/558 |

FOREIGN PATENT DOCUMENTS

| | | |
|---|---|---|
| DE | 19811517 A1 | 9/1999 |
| WO | 2010002944 A2 | 1/2010 |
| WO | 2010042273 A1 | 4/2010 |

OTHER PUBLICATIONS

International Search Report for International Application No. PCT/US2021/020445; Application Filing Date: Mar. 2, 2021; Date of Mailing: Jun. 11, 2021; 4 pages.
Reinhardt, H.J. et al., "Oxygen Enrichment for Intensification of Air Oxidation Reactions", ISBN 978-3-00-049008-8, 2015, 44 pages.
Written Opinion for International Application No. PCT/US2021/020445; Application Filing Date: Mar. 2, 2021; Date of Mailing: Jun. 11, 2021; 7 pages.

* cited by examiner

*Primary Examiner* — Sikarl A Witherspoon
(74) *Attorney, Agent, or Firm* — CANTOR COLBURN LLP

(57) ABSTRACT

A method for oxidizing a hydrocarbon includes feeding an oxidant to a top portion of a reactor; reacting the hydrocarbon with the oxidant in the reactor to obtain a reaction product stream, the reaction product stream exiting a reactor outlet at a bottom portion of the reactor; and recycling a portion of the reaction product stream to the top portion of the reactor; and introducing the oxidant into an oxidation liquid comprising the portion of the reaction product stream recycled to the top portion of the reactor to form a reaction media stream entering a reactor inlet at the top portion of the reactor. A pressure of the reactor outlet exceeds a pressure of the reactor inlet by at least 5%. The reaction media stream moves vertically downwards in the reactor.

20 Claims, 2 Drawing Sheets

METHOD AND SYSTEM FOR OXIDIZING CUMENE AND HYDROCARBONS

CROSS REFERENCE TO RELATED APPLICATIONS

This application is a National Stage application of PCT/US2021/020445, filed Mar. 2, 2021, which claims priority to and the benefit of Russian Application No. 2020109437, filed on Mar. 3, 2020, the content of each of which in its entirety is herein incorporated by reference.

BACKGROUND

The cumene process synthesizes phenol and acetone from benzene and propylene. Other reactants in the process are oxygen and a radical initiator.

More specifically, cumene can be formed by alkylation of benzene by propylene. Benzene and propylene are compressed together in the presence of a catalyst, and cumene is oxidized in air, which removes the tertiary benzylic hydrogen from cumene and forms a cumene radical. The cumene radical bonds with an oxygen molecule to give a cumene peroxide radical, which in turn forms cumene hydroperoxide ($C_6H_5C(CH_3)_2$—O—O—H) (CHP) by abstracting a benzylic hydrogen from another cumene molecule. This cumene converts into a cumene radical and feeds back into subsequent chain formations of cumene hydroperoxides. CHP is then decomposed in an acidic medium to give phenol and acetone. First, the terminal hydroperoxyl oxygen atom is pronated. This is followed by water molecule elimination and the phenyl group migrating from the benzyl carbon to the adjacent oxygen, producing a stabilized tertiary carbocation. The resulting carbocation is then attacked by water, a proton is transferred from the hydroxy oxygen to the ether oxygen, and the ion falls apart into phenol and acetone.

SUMMARY

Disclosed, in various embodiments, are improved methods and systems for oxidizing hydrocarbons and improved methods for oxidizing cumene.

The present disclosure provides a method for oxidizing a hydrocarbon including feeding an oxidant to a top portion of a reactor; reacting the hydrocarbon with the oxidant in the reactor to obtain a reaction product stream, the reaction product stream exiting a reactor outlet at a bottom portion of the reactor; recycling a portion of the reaction product stream to the top portion of the reactor; and introducing the oxidant into an oxidation liquid comprising the portion of the reaction product stream recycled to the top portion of the reactor to form a reaction media stream entering a reactor inlet at the top portion of the reactor. A pressure of the reactor outlet exceeds a pressure of the reactor inlet by at least 5%. The reaction media stream moves vertically downwards in the reactor, and a downward movement linear velocity of the oxidation liquid exceeds a floating linear velocity of the oxidant in the oxidation liquid, thereby providing downwards movement of the oxidant in the reactor.

The present disclosure provides a system for oxidizing cumene including a reactor for reacting the cumene and an oxidant to obtain a reaction product stream, the reactor including an oxidant inlet at a top portion of the reactor; and a pump in fluid communication with the top portion of the reactor and a bottom portion of the reactor for recycling a portion of the reaction product stream to the top portion of the reactor from the bottom portion of the reactor.

The present disclosure provides a method for oxidizing cumene including feeding an oxidant to a top portion of a reactor; reacting the cumene with the oxidant in the reactor to obtain a reaction product stream including cumene hydroperoxide, the reaction product stream exiting a reactor outlet at a bottom portion of the reactor; recycling a portion of the reaction product stream to the top portion of the reactor; and introducing the oxidant into an oxidation liquid comprising the portion of the reaction product stream recycled to the top portion of the reactor to form a reaction media stream entering a reactor inlet at the top portion of the reactor. A pressure of the reactor outlet exceeds a pressure of the reactor inlet pressure by at least 5%. The reaction media stream moves downwards in the reactor.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Figure 1B:
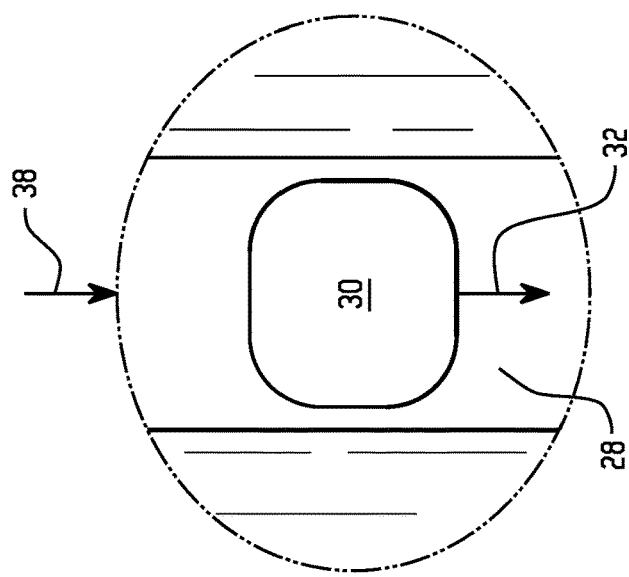
FIG. 1B is a detailed view of a section of FIG. 1A.

In the production of phenol and acetone, cumene oxidation can consume more power than any other stage. While the oxidation reaction may be exothermic, such relatively low-potential heat may not be readily utilized, and relatively high power may be required for air compression (e.g., to compress the air that is input to the process), which can make up approximately two-thirds of total electric power consumption of the process. Desired are improved methods for oxidizing a hydrocarbon, and more specifically, improved methods for oxidizing cumene.

The present disclosure provides improved methods and systems for oxidizing hydrocarbons (e.g., improved methods for oxidizing cumene). More particularly, the present disclosure provides that oxidation reaction gas pumping from the top portion of the reactor to the bottom portion of the reactor can provide improved pressure usage in that oxygen rich gas at lower pressure can be introduced to the top portion of the reactor, and the pressure of this introduced gas gradually increases while moving to the bottom portion of the reactor while the oxygen concentration decreases. This feature provides a lower oxygen partial pressure drop for the reactor as compared to conventional reactors utilizing upward gas movement. Such an advantageous approach of the present disclosure can provide improved oxidation conditions for the reactor at lower pressure of the introduced oxygen rich gas, and also thereby saving power consumption due to the reduced air compression of the introduced oxygen rich gas at lower pressure. The reactor can be, for example, a tube-type reactor, or a vessel equipped with a heat exchanger, providing free movement of a reaction mixture stream vertically from top to bottom and linear velocity faster than gas bubbles floating upward.

Current practice provides that compressors provide compressed air for the oxidation process, and the hydrostatic pressure in the bottom of the oxidation reactor can be nearly 3 bars (300 kiloPascals (kPa)). This feature in conjunction with oxygen-containing (e.g., oxidizing) gas movement from the bottom to the top of a conventional reactor can result in a higher pressure and higher oxygen concentration in the bottom of the reactor compared to the pressure and oxygen concentration in the top of the reactor. Stated another way, conventional practice provides that there can be an oxygen deficit in the top of the reactor and excess oxygen in the bottom of the reactor. This can result in the need to excessively compress the oxygen feed (e.g., air input) that is fed to the bottom of the reactor, in order to provide satisfactory oxidation conditions later in the process in the top of the reactor. With the advantageous methods disclosed herein, excessive air compression and/or energy consumption can be substantially reduced or avoided by providing for gas input and gas movement from the top of the reactor to the bottom of the reactor.

Cumene oxidation generally occurs in serially connected reactors, wherein a cumene oxidation product passes through each reactor individually and cumene hydroperoxide concentration in the reactor effluent gradually increases, reaching 25 to 30% CHP concentration after the final reactor. The same can be said for hydrocarbon oxidation. Reactor operating pressure can vary from 2 to 6 bars (200 to 600 kPa) at the top reactor outlet. Additional hydrostatic pressure adds to these values at the bottom of the reactor, making the air inlet pressure 3-9 bars (300-900 kPa). The air inlet pressure is provided by an air compressor, consuming 50 to 70% of the total electric power of the entire process. The air compressor operates in adiabatic or close to adiabatic conditions, resulting in excessive power consumption and thus, high energy spending on compressed air heating. This excessive heat must be removed before the air is fed into the oxidation reactor, since the air temperature after the compressor is much higher than the oxidation reactor temperature, resulting in the necessity of an additional heat exchanger to provide the desired compressed air temperature.

Cumene oxidation selectivity has a maximum value at intermediate oxygen partial pressure with cumene oxidation with air taking place in conditions of variable oxygen concentration. Fresh air as referred to herein, generally refers to air having an $O_2$ concentration of 20.9 volume percent (vol %), based on a total volume of air. Reactor exhaust gas can contain 2 to 5 vol % $O_2$. Overall pressure in the reactor can decrease from 3 to 9 bars to 2 to 6 bars (300 to 900 kPa to 200 to 600 kPa) which also increases the oxygen partial pressure difference between the reactor inlet and the reactor outlet. An overall higher pressure can lead to higher productivity, while an overall lower pressure can lead to higher selectivity. Difficulties can arise in creating a balance between the two.

The present disclosure advantageously provides that by having the reactor outlet pressure higher than the reactor inlet pressure, this can assist in achieving desired, e.g., optimal, values for pressure and selectivity within the reactor. For example, the present disclosure provides that reactor outlet pressure can exceed the reactor inlet pressure by at least 5%, for example, by at least 10%, such as by at least 25%, by at least 50%, or by at least 100%.

A more complete understanding of the components, processes, and apparatuses disclosed herein can be obtained by reference to the accompanying drawings. These figures (also referred to herein as "FIG.") are merely schematic representations based on convenience and the ease of demonstrating the present disclosure, and are, therefore, not intended to indicate relative size and dimensions of the devices or components thereof and/or to define or limit the scope of the exemplary embodiments. Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

Figure 1A:
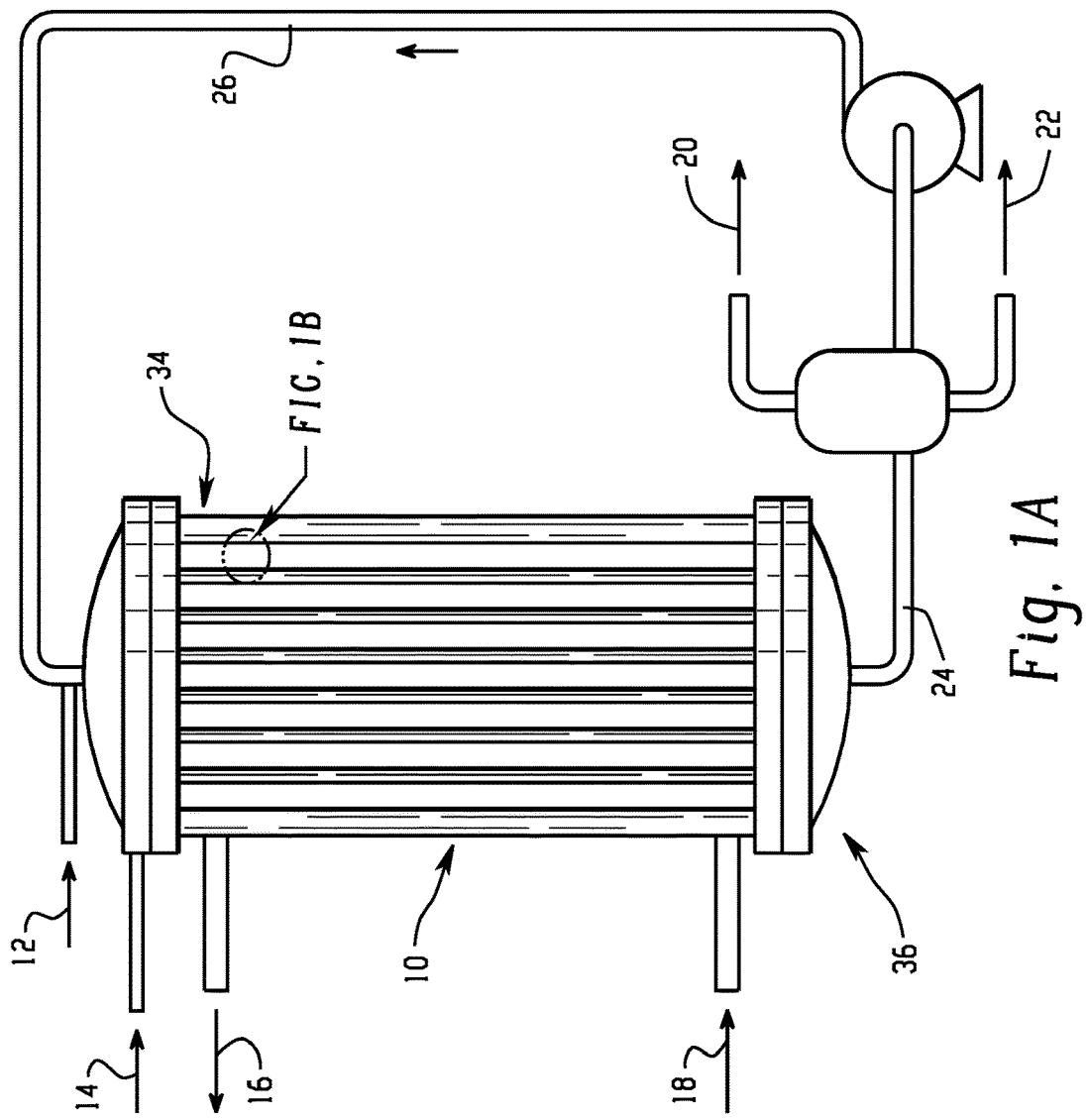
FIG. 1A is a view of an oxidation reactor with downward flow.

FIG. 1A shows an oxidation reactor 10 with downward flow. FIG. 1B is an exploded view of a section of FIG. 1A. The oxidation reactor 10 can be utilized to oxidize a material including, but not limited to, hydrocarbons (e.g., cumene). As shown in FIG. 1A, an oxidant (e.g., oxidation gas; oxygen-containing gas such as air) can be fed to the oxidation reactor 10 via an oxidant line 14 at a top portion 34 of the oxidation reactor 10. A feedstream 12 including hydrocarbon(s) (e.g., cumene and/or CHP) can be reacted with the oxidant in the reactor 10 to obtain a reaction product stream 24. Water can be fed into the reactor 10 at water line 18 and removed from the reactor 10 at water line 16.

The reaction product stream 24 exits at a bottom portion 36 of the reactor 10. A portion of the reaction product stream 24 can be separated to obtain an exhaust gas stream 20 and a liquid product stream 22. The liquid product stream 22 can include ethylbenzene, cumene, cumene hydroperoxide, ethylbenzene hydroperoxide, or a combination comprising at least one of the foregoing.

A portion of the reaction product stream 24 can be recycled to the top portion 34 of the oxidation reactor 10 via recycle stream 26. The oxidant that is fed from oxidant line 14 can be introduced into an oxidation liquid 28 including the recycle stream 26 at top portion 34 of the oxidation reactor 10 to thereby form a reaction media stream 38. As shown in FIG. 1B, reaction media stream 38 includes oxidation liquid 28 including recycle stream 26 and/or feedstream 12, and reaction media stream 38 includes oxidation gas 30 from oxidant line 14.

In FIG. 1B, oxidation liquid 28 and oxidation gas 30 of reaction media stream 38 are shown, with the oxidation liquid 28 and oxidation gas 30 of reaction media stream 38 moving downward in the reactor 10, shown by line 32.

According to the methods disclosed herein, oxidant/air compression inside the reactor 10 can be isothermal instead of adiabatic (adiabatic compression can occur in a conventional air compressor). This can be accomplished by moving the reaction media stream 38 downwards in the reactor 10. By moving the oxidation liquid 28 of the reaction media stream 38 downwards in the reactor, the linear velocity of the oxidation liquid 28 of the reaction media stream 38 can exceed the floating linear velocity (e.g., floating bubble) of the oxidation gas 30 relative to, e.g., in, the oxidation liquid 28, thereby providing downward movement of the oxidation gas 30. Simultaneously, hydrostatic pressure of the oxidation liquid 28 of the reaction media stream 38 can compress the oxidation gas 30, thereby making the oxygen pressure higher. Advantageously, movement of the bubbles of the oxidant gas 30 with the oxidation liquid 28 can provide more efficient gas compression. Since the bubbles of the oxidant gas 30 are in close contact with the oxidation liquid 28 during the method, compression becomes isothermal instead of adiabatic, significantly reducing energy consumption. For example, energy consumption can be reduced by approximately 50% with the methods described herein. As such, an extra heat exchanger may not be needed to maintain the gas at the proper temperature. The air compressor can maintain a temperature of 1 to 5 bars (100 to 500 kPa) or 2 to 6 bars (200 to 600 kPa), which is lower than that of a traditional oxidation reactor. Exhaust gas (e.g., oxygen poor gas) increases with a higher pressure than the inlet, so more energy can be recovered from the exhaust gas, contributing to the reduction in energy consumption.

Accordingly, a method for oxidizing a hydrocarbon can include feeding an oxidant to a top portion 34 of a reactor 10. The hydrocarbon can be reacted with the oxidant in the reactor 10 to obtain a reaction product stream 24. The reaction product stream 24 can exit a bottom portion 36 of the reactor 10. A reactor 10 outlet pressure can exceed a reactor 10 inlet pressure by at least 5%.

A portion of the reaction product stream 24 can be recycled to the top portion 34 of the oxidation reactor 10 via recycle stream 26, and the oxidant that is fed from oxidant line 14 at top portion 34 of the reactor 10 can be introduced into the oxidation liquid 28 including the recycle stream 26 to thereby form a reaction media stream 38. The reaction media stream 38 can move vertically downward in the reactor 10. A downward movement linear velocity of the oxidation liquid 28 can exceed a floating linear velocity of the oxidation gas 30 relative to, e.g., in, the oxidation liquid 28 of reaction media stream 38. This can provide downwards movement of the oxidant in the reactor 10.

The present disclosure also provides for a method for oxidizing cumene including feeding an oxidant to a top portion 34 of a reactor 10. The cumene can be reacted with the oxidant in the reactor 10 to obtain a reaction product stream 24. The reaction product stream 24 can comprise CHP. The reaction product stream 24 can exit a bottom portion 36 of the reactor 10. A reactor 10 outlet pressure can exceed a reactor 10 inlet pressure by at least 5%. The reactor 10 outlet pressure can be a pressure at a reactor 10 outlet at which the reaction product stream 24 exits the reactor 10 at a bottom portion 36 of the reactor 10. The reactor 10 inlet pressure can be a pressure at a reactor 10 inlet at which the reaction media stream 38 enters the reactor 10 at the top portion 34 of the reactor 10.

A portion of the reaction product stream 24 can be recycled to the top portion 34 of the reactor 10, via recycle stream 26, to form reaction media stream 38. The reaction media stream 38 can move vertically downward in the reactor 10. A downward movement linear velocity of the oxidation liquid 28 can exceed a floating linear velocity of the oxidation gas 30 relative to, e.g., in, the oxidation liquid 28, thereby providing downwards movement of the oxidant in the reactor 10.

The oxidant can comprise air. The oxidant can be compressed before being fed to the top portion 34 of the reactor 10. The downward movement linear velocity of oxidation liquid 28 of reaction media stream 38 can be 0.2 to 2 meters per second, for example, 0.3 to 1 meters per second, for example, 0.4 to 0.8 meters per second. The oxidation gas 30 (e.g., air bubble) floating linear velocity can be 0.1 to 0.15 meters per second in still cumene/CHP.

The oxidant can be fed to the reactor 10 at an oxidant pressure of less than or equal to 200 kiloPascals (kPa), for example less than or equal to 185 kPa, for example, less than or equal to 170 kPa. The present disclosure provides that the oxidant (e.g., oxidation gas) can be compressed using circulation pump power, and operating conditions are close to isothermal. In contrast, it is noted that air being compressed with a conventional compressor, providing an adiabatic efficiency of 75%, at 170 kPa, requires heating the air to 90° C.; and at 185 kPa, the air must be heated to 100° C.; and at 200 kPa, the air must be heated to 110° C. This requires air cooling before the reactor, which is not desired. Moreover, with conventional methods without downward flow, the oxidation gas is compressed using air compressors that operate close to adiabatic conditions, thereby consuming extra energy.

The reaction product stream 24 can be separated into a liquid product stream 22 (e.g., containing reaction media) and an exhaust gas stream 20. The liquid product stream 22 can comprise ethylbenzene in a hydrocarbon oxidation process. The liquid product stream 22 can comprise cumene hydroperoxide, cumene, or a combination comprising at least one of the foregoing in a cumene oxidation process. The oxidant can comprise oxygen-containing gas. The process can comprise adding to the reactor 10 hydrogen peroxide, dioxygen, ozone, an anthraquinone, a $C_{2-32}$ alkyl peroxide, a $C_{2-32}$ alkyl hydroperoxide, a $C_{2-32}$ ketone peroxide, a $C_{2-32}$ diacyl peroxide, a $C_{3-22}$ diperoxy, a ketal, a $C_{2-32}$ peroxyester, a $C_{2-32}$ peroxydicarbonate, a $C_{2-32}$ peroxy acid, a $C_{6-32}$ perbenzoic acid, a $C_{2-32}$ peracid, a periodinane, a periodate, or a combination comprising at least one of the foregoing.

The reacting of the hydrocarbon with the oxidant in the reactor 10 can occur at a temperature of 75° C. to 135° C., for example, 80° C. to 120° C., for example, 85° C. to 115° C.

A reaction product can be produced. The reaction product can include phenol, acetone, ethylene, or a combination comprising at least one of the foregoing.

A system for oxidizing a hydrocarbon (e.g., cumene) can include a reactor 10 for reacting the hydrocarbon (e.g., cumene). The reactor 10 can include an oxidant inlet 14 at a top portion 34 of the reactor 10. The reactor 10 can include a pump in fluid communication with the top portion 34 of the reactor 10 and a bottom portion 36 of the reactor 10 for recycling a portion of the reaction product stream 24 to the top portion 34 of the reactor 10 from the bottom portion 36 of the reactor 10. The reactor 10 can further include a compressor in fluid communication with the oxidant for compressing the oxidant before being fed to the oxidant inlet 14.

The reaction product stream 24 exits at a bottom portion 36 of the reactor 10. A portion of the reaction product stream 24 can be separated to obtain an exhaust gas stream 20 and a liquid product stream 22. The liquid product stream 22 can include ethylbenzene, cumene, cumene hydroperoxide, ethylbenzene hydroperoxide, or a combination comprising at least one of the foregoing.

The following example are merely illustrative of the methods and system disclosed herein and are not intended to limit the scope hereof. Unless otherwise stated, all examples were based upon simulations.

EXAMPLES

In the following Example and Comparative Example, energy savings using the methods disclosed herein are calculated assuming the conditions summarized in Table 1. The energy savings are calculated based upon the stream system shown in FIG. 2. Production was measured in kilograms per hour (kg/h), pressure in kiloPascals (kPa), air flow in kg/h, density in kilograms per cubic meter (kg/m$^3$), volume in cubic meters per hour (m$^3$/h), and power in kilowatts (kW).

Figure 2:
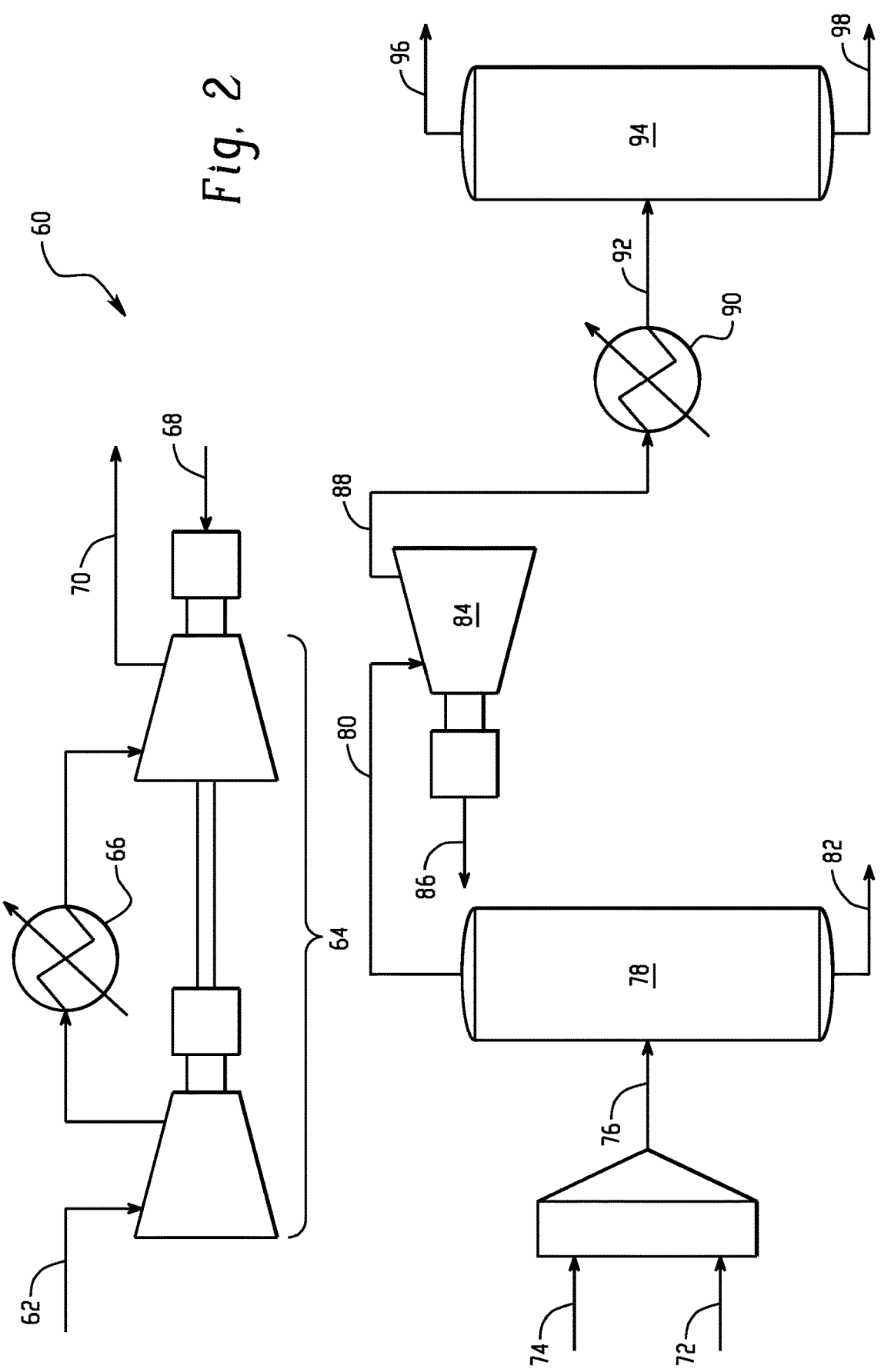
FIG. 2 is a schematic overview of a system and method for producing hydrocarbons or cumene.

FIG. 2 shows an example stream system 60 used in oxidation gas processing. In FIG. 2, a fresh air stream 62 is compressed in a compressor 64 and then passed through an intermediate cooler 66 to remove some heat. The fresh air stream 62 consumes electric power at line 68 and provides compressed air 70 for oxidation. A spent air stream 72 is mixed with an oxidized cumene stream 74 to make an oxidation mass stream 76. The oxidation mass stream 76 is separated in column 78 into two streams, a first stream 80 and a second stream 82. The first stream 80 can include spent air saturated with oxidation products and the second stream 82 can include oxidation mass liquid. The first stream 80 can pass through the expander 84, which returns power from the first stream 80 (e.g., compressed stream) via line 86 providing a spent air stream 88. The spent air stream 88 passes through a cooler 90 to remove some heat from the spent air stream 88. Cold exhaust air stream 92 separates in a separator 94 into an exhaust gas stream 96 and an exhaust air condensate stream 98. This stream system 60 can allow for estimating energy streams in an oxidation system.

TABLE 1

Calculation Base Parameters

| | |
|---|---|
| Phenol production | 40,000 kg/h |
| CHP production | 64,686 kg/h |
| Cumene | 52,400 kg/h |

TABLE 1-continued

Calculation Base Parameters

| | |
|---|---|
| Circulation pump: | |
| Liquid/Gas volume ratio at the top of the reactor* | 4:1 |
| Reactor top pressure | 403 kPa |
| Pump inlet pressure | 603 kPa |
| Pump outlet pressure | 653 kPa |
| Air flow | 75,379 kg/h |
| Gas density | 4.7 kg/m$^3$ |
| Gas volume | 16,038 m$^3$/h |
| Delta Power | 891 kW |

*Liquid/Gas volume ratio increases with movement of the reaction mixture from the top of the reactor to the bottom of the reactor because of gas compression (gas volume reduces at the bottom).

Table 2 shows material streams data in a cumene oxidation system simulation, while Table 3 shows energy streams data in a cumene oxidation system simulation. Temperature is measured in degrees Celsius (° C.), pressure in kPa, molar flow in kilogram-moles per hour (kg·mol/h), mass flow in kilograms per hour (kg/h), volumetric flow (liquid) in cubic meters per hour (m$^3$/h), and heat flow in kilojoules per hour (kJ/h). In Table 3, power is measured in kJ/h, kW, and horsepower (hp). DMBA in Table 2 refers to dimethyl benzyl alcohol.

TABLE 2

Material Streams in Cumene Oxidation System Simulations

| Stream | 62 | 80 | 88 | 74 | 72 |
|---|---|---|---|---|---|
| Vapor fraction | 1 | 1 | 0.982068 | 0 | 1 |
| Temperature, ° C. | 20 | 97 | 41 | 111 | 109 |
| Pressure, kPa | 101.3 | 653 | 160 | 653 | 653 |
| Molar flow, kg·mol/h | 2,827.634601 | 2,768.480183 | 2,768.48 | 531.9739 | 2,702.526 |
| Mass flow, kg/h | 80,740.27034 | 84,077.25081 | 84,077.25 | 64,700 | 75,379.21 |
| Vol. flow liquid, m$^3$/h | 93.87316585 | 102.4070331 | 102.407 | 73.99636 | 92.38394 |
| Heat flow, kJ/h | −13593848.7 | −7355614.262 | −1.5E+07 | −1.9E+07 | −8095493 |
| Water | 1.94E−02 | 2.08E−02 | 2.08E−02 | 0 | 2.27E−02 |
| Nitrogen | 0.796432161 | 0.926623671 | 0.926624 | 0 | 0.950648 |
| Oxygen | 0.184216379 | 2.60E−02 | 2.60E−02 | 0 | 2.66E−02 |
| Cumene | 0 | 2.58E−02 | 2.58E−02 | 0.910696 | 0 |
| DMBA | 0 | 7.77E−04 | 7.77E−04 | 8.93E−02 | 0 |

| Stream | 76 | 82 | 96 | 98 | 70 |
|---|---|---|---|---|---|
| Vapor fraction | 0.855922 | 0 | 1 | 0 | 1 |
| Temperature, ° C. | 97 | 97 | 29 | 29 | 93 |
| Pressure, kPa | 653 | 653 | 159 | 159 | 403 |
| Molar flow, kg·mol/h | 3,234.5 | 466.0199 | 2,704.657 | 63.82316 | 2,827.635 |
| Mass flow, kg/h | 140,079.2 | 56,001.96 | 76,681.1 | 7,396.146 | 80,740.27 |
| Vol. flow liquid, m$^3$/h | 166.3803 | 63.97326 | 93.89768 | 8.509352 | 93.87317 |
| Heat flow, kJ/h | −2.7E+07 | −2E+07 | −1.3E+07 | −3596507 | −7487666 |
| Water | 1.90E−02 | 7.96E−03 | 2.02E−02 | 4.59E−02 | 1.94E−02 |
| Nitrogen | 0.794296 | 8.18E−03 | 0.948455 | 1.47E−03 | 0.796432 |
| Oxygen | 2.23E−02 | 1.44E−04 | 2.66E−02 | 2.44E−05 | 0.184216 |
| Cumene | 0.149781 | 0.886391 | 4.68E−03 | 0.92044 | 0 |
| DMBA | 1.47E−02 | 9.73E−02 | 3.57E−05 | 3.22E−02 | 0 |

TABLE 3

Energy Streams in Cumene Oxidation System Simulation

| | Energy Consumed 68 | Energy Recovered 86 | Intermediate Cooler 90 | Cooler 66 | Circulation pump | Total electric power |
|---|---|---|---|---|---|---|
| Power, kJ/hr | 1,4866,182 | 7,354,723 | 1,700,000 | 8,760,000 | | |
| kW | 4,130 | 2,043 | 472 | 2,433 | 891 | 2,978 (3,715*) |
| hp | 5,536 | 2,739 | | | 1,194 | 3,991 (4,980*) |

*In the simulation, 150 hp of power was recovered in the expander 84

The energy streams for the conventional process without downward flow are calculated using the following operating conditions as reference: air to oxidizers are operated at 80,739 kg/h, a temperature of 93° C., and a pressure of 862 kPa. The oxidation reactor exhaust gas is operated at 75,378 kg/h, a temperature of 97° C., and a pressure of 552 kPa. The results are shown in Table 4.

TABLE 4

Energy Streams in Cumene Oxidation System Simulation

|  | Energy Consumed | Energy Recovered | Intermediate Cooler | Cooler | Total electric power |
|---|---|---|---|---|---|
| Power, kJ/hr | 28,128,662 | 4,701,600 | 1,700,000 | 22,030,000 |  |
| kW | 7,814 | 1,306 | 472 | 6,119 | 6,508 |
| hp | 10,474 | 1,750 |  |  | 8,724 |

The data in Tables 3 and 4 assumes the same exhaust gas conditions. However, Table 3 provides results of the method as described herein with the advantageous downward flow, and Table 4 provides results of a Comparative Example without downward flow.

The method of the present disclosure with the downward flow operates at lower reactor pressure because the gas outlet is at the reactor bottom pressure. The oxidation gas is compressed using circulation pump power, and operating conditions are close to isothermal.

In contrast, in the comparative method without downward flow, the oxidation gas is compressed using air compressors which operate close to adiabatic conditions, consuming extra energy. This is seen in energy consumed (10,474 hp for the comparative method without downward flow versus 5,536 hp for the method of the present disclosure with the downward flow); energy recovered (1,750 hp versus 2,739 hp); and total electric power (8,724 hp versus 3,991 hp) as shown in Tables 3 and 4. As can be seen from Tables 3 and 4, the total electric power of a cumene oxidation system including a downward flow reactor design (3,991 hp) is at least 50% less than the total electric power of a cumene oxidation system including a traditional oxidation reactor design without downward flow (8,724 hp). Comparative reactors can operate at 200 kPa to 500 kPa at the top of the reactor (reactor outlet) and 400 kPa to 800 kPa, for example, 400 kPa to 600 kPa, at the bottom of the reactor (reactor inlet)

The methods and system disclosed herein include(s) at least the following aspects:

Aspect 1: A method for oxidizing a hydrocarbon, comprising: feeding an oxidant to a top portion of a reactor; reacting the hydrocarbon with the oxidant in the reactor to obtain a reaction product stream, the reaction product stream exiting a reactor outlet at a bottom portion of the reactor; recycling a portion of the reaction product stream to the top portion of the reactor; and introducing the oxidant into an oxidation liquid comprising the portion of the reaction product stream recycled to the top portion of the reactor to form a reaction media stream entering a reactor inlet at the top portion of the reactor; wherein a pressure of the reactor outlet exceeds a pressure of the reactor inlet pressure by at least 5%; wherein the reaction media stream moves vertically downwards in the reactor; and wherein a downward movement linear velocity of the oxidation liquid exceeds a floating linear velocity of the oxidant in the oxidation liquid, thereby providing downwards movement of the oxidant in the reactor.

Aspect 2: The method of Aspect 1, wherein the downward movement linear velocity of the oxidation liquid is 0.2 to 2 meters per second, such as 0.3 to 1 meters per second or 0.4 to 0.8 meters per second.

Aspect 3: The method of any one of the preceding aspects, wherein the oxidant is fed to the reactor at an oxidant pressure of less than or equal to 200 kiloPascals, such as less than or equal to 185 kiloPascals or less than or equal to 170 kiloPascals.

Aspect 4: The method of any one of the preceding aspects, further comprising compressing the oxidant before feeding the oxidant to the top portion of the reactor.

Aspect 5: The method of any one of the preceding aspects, further comprising separating the reaction product stream to obtain a liquid product stream and an exhaust gas stream.

Aspect 6: The method of Aspect 5, wherein the liquid product stream comprises a hydrocarbon oxidation product.

Aspect 7: The method of Aspect 5, wherein the liquid product stream comprises ethylbenzene.

Aspect 8: The method of any one of the preceding aspects, wherein the oxidant comprises oxygen-containing gas.

Aspect 9: A reaction product produced by the method of any one of Aspects 1 to 8.

Aspect 10: A system for oxidizing cumene, comprising: a reactor for reacting the cumene and an oxidant to obtain a reaction product stream, the reactor comprising an oxidant inlet at a top portion of the reactor; and a pump in fluid communication with the top portion of the reactor and a bottom portion of the reactor for recycling a portion of the reaction product stream to the top portion of the reactor from the bottom portion of the reactor.

Aspect 11: The system of Aspect 10, further comprising a compressor in fluid communication with the oxidant inlet for compressing the oxidant before the oxidant is fed to the oxidant inlet.

Aspect 12: A method for oxidizing cumene, comprising: feeding an oxidant to a top portion of a reactor; reacting the cumene with the oxidant in the reactor to obtain a reaction product stream comprising cumene hydroperoxide, the reaction product stream exiting a reactor outlet at a bottom portion of the reactor; recycling a portion of the reaction product stream to the top portion of the reactor; and introducing the oxidant into an oxidation liquid comprising the portion of the reaction product stream recycled to the top portion of the reactor to form a reaction media stream entering a reactor inlet at the top portion of the reactor; wherein a pressure of the reactor outlet exceeds a pressure of the reactor inlet by at least 5%, and wherein the reaction media stream moves downwards in the reactor.

Aspect 13: The method of Aspect 12, wherein the oxidant comprises air.

Aspect 14: The method of Aspect 12 or Aspect 13, wherein a downward movement linear velocity of the oxidation liquid exceeds a floating linear velocity of the oxidant in the oxidation liquid, thereby providing downwards movement of the oxidant in the reactor.

Aspect 15: The method of Aspect 14, wherein the downward movement linear velocity of the oxidation liquid is 0.2 to 2 meters per second, such as 0.3 to 1 meters per second or 0.4 to 0.8 meters per second.

Aspect 16: The method of any of Aspects 12 to 15, wherein the oxidant is fed to the reactor at an oxidant pressure of less than or equal to 200 kiloPascals, such as less than or equal to 185 kiloPascals or less than or equal to 170 kiloPascals.

Aspect 17: The method of any of Aspects 12 to 16, further comprising compressing the oxidant before feeding the oxidant to the top portion of the reactor.

Aspect 18: The method of any of Aspects 12 to 17, further comprising separating the reaction product stream to obtain a liquid product stream and an exhaust gas stream.

Aspect 19: The method of Aspect 18, wherein the liquid product stream comprises cumene hydroperoxide, cumene, or a combination comprising at least one of the foregoing.

Aspect 20: The method of any of Aspects 12 to 19, wherein the reacting is at a temperature of 75° C. to 135° C., such as 80° C. to 120° C. or 85° C. to 115° C.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for oxidizing a hydrocarbon, comprising:
    feeding an oxidant to a top portion of a reactor;
    reacting the hydrocarbon with the oxidant in the reactor to obtain a reaction product stream, the reaction product stream exiting a reactor outlet at a bottom portion of the reactor;
    recycling a portion of the reaction product stream to the top portion of the reactor; and
    introducing the oxidant into an oxidation liquid comprising the portion of the reaction product stream recycled to the top portion of the reactor to form a reaction media stream entering a reactor inlet at the top portion of the reactor;
    wherein a pressure of the reactor outlet exceeds a pressure of the reactor inlet by at least 5%;
    wherein the reaction media stream moves vertically downwards in the reactor; and
    wherein a downward movement linear velocity of the oxidation liquid exceeds a floating linear velocity of the oxidant in the oxidation liquid, thereby providing downwards movement of the oxidant in the reactor.

2. The method of claim 1, wherein the downward movement linear velocity of the oxidation liquid is 0.2 to 2 meters per second.

3. The method of claim 1, wherein the oxidant is fed to the reactor at an oxidant pressure of less than or equal to 200 kiloPascals.

4. The method of claim 1, further comprising compressing the oxidant before feeding the oxidant to the top portion of the reactor.

5. The method of claim 1, further comprising separating the reaction product stream to obtain a liquid product stream and an exhaust gas stream.

6. The method of claim 5, wherein the liquid product stream comprises a hydrocarbon oxidation product.

7. The method of claim 5, wherein the liquid product stream comprises ethylbenzene.

8. The method of claim 1, wherein the oxidant comprises oxygen-containing gas.

9. A system for oxidizing cumene, comprising:
    a reactor for reacting the cumene and an oxidant to obtain a reaction product stream, the reactor comprising an oxidant inlet at a top portion of the reactor; and
    a pump in fluid communication with the top portion of the reactor and a bottom portion of the reactor for recycling a portion of the reaction product stream to the top portion of the reactor from the bottom portion of the reactor providing downward movement of the oxidant in the reactor.

10. The system of claim 9, further comprising a compressor in fluid communication with the oxidant inlet for compressing the oxidant before the oxidant is fed to the oxidant inlet.

11. A method for oxidizing cumene, comprising:
feeding an oxidant to a top portion of a reactor;
reacting the cumene with the oxidant in the reactor to obtain a reaction product stream comprising cumene hydroperoxide, the reaction product stream exiting a reactor outlet at a bottom portion of the reactor;
recycling a portion of the reaction product stream to the top portion of the reactor; and
introducing the oxidant into an oxidation liquid comprising the portion of the reaction product stream recycled to the top portion of the reactor to form a reaction media stream entering a reactor inlet at the top portion of the reactor;
wherein a pressure of the reactor outlet exceeds a pressure of the reactor inlet by at least 5%; and
wherein the reaction media stream moves downwards in the reactor.

12. The method of claim 11, wherein the oxidant comprises air.

13. The method of claim 11, wherein a downward movement linear velocity of the oxidation liquid exceeds a floating linear velocity of the oxidant in the oxidation liquid, thereby providing downwards movement of the oxidant in the reactor.

14. The method of claim 13, wherein the downward movement linear velocity of the oxidation liquid is 0.2 to 2 meters per second.

15. The method of claim 11, wherein the oxidant is fed to the reactor at an oxidant pressure of less than or equal to 200 kiloPascals.

16. The method of claim 11, further comprising compressing the oxidant before feeding the oxidant to the top portion of the reactor.

17. The method of claim 11, further comprising separating the reaction product stream to obtain a liquid product stream and an exhaust gas stream.

18. The method of claim 17, wherein the liquid product stream comprises cumene hydroperoxide, cumene, or a combination comprising at least one of the foregoing.

19. The method of claim 11, wherein the reacting is at a temperature of 75° C. to 135° C.

20. The system of claim 9, wherein:
the pump provides a downward movement linear velocity to the oxidant; and
the downward movement linear velocity exceeds a floating linear velocity of the oxidant in an oxidation liquid comprising the portion of the reaction product stream recycled to the top portion of the reactor, thereby moving the oxidant downwards in the reactor.

* * * * *